United States Patent
Fifolt et al.

(10) Patent No.: US 6,284,934 B1
(45) Date of Patent: *Sep. 4, 2001

(54) REDUCING META CONTENT OF ISOMERIC MIXTURES OF HALO SUBSTITUTED ALKYLBENZENES

(75) Inventors: Michael J. Fifolt; William S. Derwin, both of Grand Island; Viesturs Lesins, Tonawanda; Arthur H. Morth, Grand Island; Frank P. Bermel, Orchard Park; David Y. Tang, Amherst; Mark E. Lindrose, Buffalo; William L. Rueter, Niagara Falls, all of NY (US)

(73) Assignee: Occidental Chemical Corporation, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 26 days.

(21) Appl. No.: 09/480,382

(22) Filed: Jan. 10, 2000

Related U.S. Application Data

(63) Continuation-in-part of application No. 09/193,755, filed on Nov. 17, 1998, now Pat. No. 6,130,361.

(51) Int. Cl.[7] .................................................. C07C 17/38
(52) U.S. Cl. ............................................................ 570/211
(58) Field of Search .............................................. 570/211

(56) References Cited

U.S. PATENT DOCUMENTS 4,827,058 * 5/1989 Mais et al. ........................... 570/211

* cited by examiner

Primary Examiner—Alan Siegel
(74) Attorney, Agent, or Firm—Richard D. Fuerle; Anne E. Brookes

(57) ABSTRACT

Disclosed is a method of separating the meta isomer of a haloalkylbenzene having the general formula from a mixture with at least one other isomer, where X is Cl or Br and R is alkyl from $C_2$ to $C_{12}$ or cycloalkyl from $C_3$ to $C_8$. About 0.0001 to about 5 wt % of a Friedel-Crafts catalyst is added to the mixture and the mixture is exposed to a brominating agent which preferentially brominates the meta isomer. The mixture is then heated at a temperature above the boiling point of the other isomers but below the boiling point of the brominated meta isomer.

21 Claims, No Drawings

REDUCING META CONTENT OF ISOMERIC MIXTURES OF HALO SUBSTITUTED ALKYLBENZENES

This application is a continuation-in-part of application Ser. No. 09/193,755, filed Nov. 17, 1998 now U.S. Pat. No. 6,130,367 by V. Lesins et al., titled, "Reducing Meta Content of Isomeric Mixtures of Halo Substituted Toluenes."

BACKGROUND OF THE INVENTION

This invention relates to a method of reducing the content of the meta isomer of a halo substituted alkylbenzene in a mixture with other isomers. In particulars, it relates to exposing the mixture to a brominating agent under conditions such that the meta isomer is preferentially brominated.

Commercial parachloroethylbenzene (PCEB) is made by chlorinating ethylbenzene (EB). After distilling off about 20 wt % of the unreacted EB, the remaining material contains about 50 wt % orthochloroethylbenzene (OCEB), 1.5 wt % metachloroethylbenzene (MCEB), 45 wt % PCEB, and the remainder overchlorinated impurities (about 2.5 wt %). PCEB is used as an intermediate in the preparation of pharmaceuticals, paint pigments, herbicides, and other chemicals. While the presence of small amounts of the OCEB is usually innocuous, it has been found that the presence of MCEB can deleteriously affect the properties of the chemicals made from PCEB. Unfortunately, the boiling point of MCEB is close to the boiling point of PCEB and the two isomers cannot be easily separated.

In U.S. Pat. No. 4,827,058, herein incorporated by reference, a chlorotoluene isomeric mixture is chlorinated in the presence of a Friedel-Crafts catalyst at a temperature of 0° C. up to the boiling point of the mixture. The metachlorotoluene (MCT) chlorinates to dichlorotoluene to a much greater extent than does the orthochlorotoluene (OCT) or the parachlorotoluene (PCT). The PCT-OCT mixture is then separated from the higher boiling dichlorotoluenes (DCT) by distillation.

SUMMARY OF THE INVENTION

We have discovered that meta halo substituted alkylbenzenes can be separated from an isomeric mixture by exposing the mixture to a brominating agent under conditions such that the meta isomer is preferentially brominated. We have found that it is more selective for the meta isomer in this reaction than is chlorine. Thus, we are able to remove more of the meta isomer while haloginating less of the desirable para isomer than was possible using chlorine.

We have also found that the bromination reaction is unusually fast, which is a processing advantage. In addition, we have found that when the brominating agent is bromine, the byproduct, hydrogen bromide, is not evolved and can be converted in situ to additional brominating agent by adding chlorine. In this way, expensive bromine is not wasted.

DESCRIPTION OF THE PREFERRED EMBODIMENT

The starting substrate for the process of this invention is a mixture of isomers having the general formula

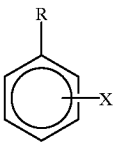

where X is Cl or Br and R is alkyl from $C_2$ to $C_{12}$ or cycloalkyl from $C_3$ to $C_8$. Preferably, X is chlorine and R is alkyl from $C_2$ to $C_6$, and most preferably R is ethyl, as those compounds are commercially more important. While the process of this invention will work with mixtures of isomers that contain almost any amount of the meta isomer, it is most practical for mixtures of isomers that contain about 0.01 to about 10 wt % of the meta isomer. Examples of mixtures of isomers that can be used in the process of this invention include chlorinated ethylbenzenes, brominated ethylbenzenes, chlorinated isopropylbenzenes, chlorinated n-butylbenzenes, chlorinated sec-butylbenzenes, chlorinated t-butylbenzenes, and brominated n-butylbenzenes; chlorinated ethylbenzenes are preferred as they are of greater commercial interest.

About 0.0001 to about 5 wt % of a Friedel-Crafts catalyst is added to the isomeric mixture. Preferably, about 0.001 to about 1 wt % catalyst is used as less is less effective and more is usually unnecessary. Examples of suitable Friedel-Crafts catalysts include the chlorides of manganese, molybdenum, titanium, iron, aluminum, zinc, tin, antimony, and mixtures thereof. The preferred catalyst is ferric chloride as it is inexpensive, works well, and is often the catalyst used to chlorinate alkylbenzenes.

It is preferable to also use about 0.001 to about 5 wt % of an optional cocatalyst. Preferably, about 0.01 to about 1 wt % of the cocatalyst is used. Examples of cocatalysts include sulfur and sulfur compounds such as diphenylsulfide, disulfur dichloride, thianthrene, thianthrene derivatives, phenoxathiin, phenoxathiin derivatives, phenothiazine, phenothiazine derivatives, iodine, and iodine compounds. The preferred cocatalyst is thianthrene as it is often used in, the chlorination of toluene.

Examples of suitable brominating agents include liquid or gaseous bromine, BrCl, and sulfuryl bromide ($S_2Br_2$). The preferred brominating agents are liquid bromine and BrCl as they are inexpensive and effective. About ½ to about 10 equivalents of brominating agent can be used per equivalent of the meta isomer that is present in the mixture. It is preferable to use about 2 to about 5 equivalents of the brominating agent per equivalent of meta isomer that is present in the mixture as less may leave some meta isomer unbrominated and more may brominate some of the para isomer. Generally, proportionally less brominating agent is required at higher meta concentrations.

If the starting material was prepared by halogenating an alkylbenzene, unreacted alkylbenzene is preferably removed first to prevent its bromination. The brominating agent is added to the mixture of isomers, catalyst, and optional cocatalyst, which can be, for example, at a temperature of about 0° C. to reflux. The preferred temperature range is between room temperature and about 50° C. as at lower temperatures the reaction is slow, although the selectivity is better, while the reverse is true at higher temperatures. The brominated agent can be added before or after the mixture is heated.

The bromination produces a bromochloro or dibromo substituted alkylbenzene and usually a halogenated byproduct, e.g., hydrogen bromide if $Br_2$ is used or HCl if BrCl is used. We have found that when bromine is used, a substantial portion of the HBr that is formed does not evolve but remains in solution. The addition of chlorine gas to the solution results in the formation of additional bromine or BrCl in situ. Thus, to prevent the evolution and loss of expensive bromine, one can use about ½ the amount of bromine, wait until it reacts, then add about the same equivalents of chlorine. The bromination reaction is unexpectedly rapid (about 15 minutes) and can be followed by gas chromatography (GC) to determine its completion. The lower boiling unreacted para and ortho isomers are then distilled off, leaving behind the higher boiling brominated meta isomer. Using the method of this invention, the meta content can be reduced to less than 0.1 wt %.

THE FOLLOWING EXAMPLES FURTHER ILLUSTRATE THIS INVENTION.

EXAMPLE 1

To a 30 L jacketed flask fitted with 2 condensers, chlorine inlet, overhead stirrer, polytetrafluoroethylene-coated thermocouple and a sub-surface sampling system was added 24,222 g of EB, 7.30 g of ferric chloride (301 ppm) and 7.25 g of a 15 wt % solution of a dialkyl thianthrene cocatalyst in OCT. The reactor system was connected to a series of water and aqueous potassium hydroxide scrubbers to trap the HCl off gas. Chlorine gas was added at an average rate of 7 L/min such that, with sufficient cooling, the reaction temperature was maintained between 40 and 42° C. for most of the reaction. The reaction was stopped with a final concentration of 21.1 wt % EB, 40.0 wt % OCEB, 1.3 wt % MCEB, 36.2 wt % PCEB and 1.42 wt % over-chlorinated impurities. Chlorine utilization was not measured but has been found to be very high under similar reaction conditions. Filtration through a Celite "Fibra-Cel SW-10" filter to remove the iron chloride gave 28,166 g. Distillation of this mixture to remove the EB gave 22,852 g with a composition of 0.15 wt % EB, 49.9 wt % OCEB, 1.57 wt % MCEB, 45.9 wt % PCEB, and 2.48 wt % over-chlorinated impurities.

This material was recharged to the clean 30 L system described above along with 6.8 g (300 ppm) ferric chloride. To this was added 2.5 mole equivalents of bromine based on the estimated moles of MCEB and EB to be removed. Thus, 1117 g (6.98 moles) of bromine were added and the reaction was stirred for 2 h at 20 to 25° C. To convert the dissolved HBr to BrCl and further react it, 496 g of chlorine were added over 2 h. The reaction mass was purged overnight with nitrogen and filtered through a Celite "Fibra-Cel SW-10" filter. Final analysis of the 24,427 g of material found 45.1 wt % OCEB, 0.0 wt % MCEB, 44.5 wt % PCEB, and 10.4 wt % chlorobromoethylbenzene and dichloroethylbenzene impurities.

EXAMPLE 2

Example 1 was repeated using 26,909 g of EB, 7.88 g (300 ppm) ferric chloride, and 7.67 g of a 15 wt % solution of a dialkyl thianthrene cocatalyst in OCT. The reaction was stopped with a final concentration of 0.20 wt % EB, 45.4 wt % OCEB, 0.90 wt % MCEB, 41.4 wt % PCEB, and 12.1 wt % over-chlorinated impurities.

This material was brominated as is, in the same way as in Example 1. Thus, 906.64 g (5.69 moles) of bromine were added in two portions and the reaction was stirred for 4 h at 20 to 25° C. Analysis of the mixture found 0.24 wt % MCEB. To convert the dissolved HBr to BrCl and further react it, 404 g of chlorine were added over 2 h. The reaction mass was purged overnight with nitrogen and filtered through a Celite "Fibra-Cel SW-10" filter. Final analysis of the 36,920 g of material found 42.7 wt % OCEB, 0.11 wt % MCEB, 40.4 wt % PCEB, and 16.8 wt % chlorobromoethylbenzene and dichloroethylbenzene impurities.

We claim:

1. A method of separating the meta isomer of an alkylbenzene having the general formula

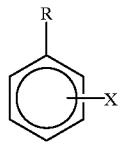

from a mixture with at least one other isomer, where X is Cl or Br and R is alkyl from $C_2$ to $C_{12}$ or cycloalkyl from $C_3$ to $C_8$, comprising
   (A) adding to said mixture about 0.0001 to about 5 wt % of a Friedel-Crafts catalyst;
   (B) exposing said mixture to about ½ to about 10 equivalents of bromine per equivalent of said meta isomer, whereby said meta isomer is preferentially brominated;
   (C) after said bromine has reacted and formed HBr adding chlorine to said mixture to react with aid HBr and from additional bromine, and
   (D) heating said mixture to a temperature above the boiling point of said other isomers but below the boiling point of said brominated meta isomer.

2. A method according to claim 1 wherein X is Cl.

3. A method according to claim 1 wherein about 0.01 to about 10 wt % of said mixture is the meta isomer.

4. A method according to claim 1 wherein said catalyst is ferric chloride.

5. A method according to claim 1 wherein 0.001 to about 5 wt % of a cocatalyst is present.

6. A method according to claim 1 wherein R is ethyl.

7. A method according to claim 1 wherein said bromination is performed at about 0° C. to reflux.

8. A method of reducing the content of metachloroethylbenzene in a mixture with parachloroethylbenzene comprising
   (A) adding to said mixture about 0.01 to about 1 wt % of a Friedel-Crafts catalyst;
   (B) heating said mixture to a temperature between 0° C. and reflux; and
   (C) adding about ¼ to about 5 equivalents of $BR_2$ to said mixture per equivalent of said metachloroethylbenzene;
   (D) after said $Br_2$ has reacted and formed HBr, adding $Cl_2$ to said mixture to react with said HBr and form additional $Br_2$; and
   (E) heating said mixture to a temperature above the boiling point of said parachloroethylbenzene but below the boiling point of said brominated metachloroethylbenzene.

9. A method according to claim 8 wherein said Friedel-Crafts catalyst is ferric chloride.

10. A method according to claim 8 wherein said mixture includes about 0.01 to about 1 wt % of a cocatalyst.

11. A method according to claim 10 wherein said cocatalyst is thianthrene.

12. A method of reducing the content of a metachloroalkylbenzene having the general formula

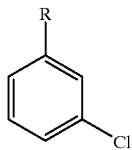

where R is alkyl from $C_2$ to $C_6$ in a mixture with its parachloroalkylbenzene isomer comprising (A) adding to said mixture about 0.01 to about 1 wt % of a Friedel-Crafts catalyst;

(B) heating said mixture to a temperature between 0° C. and reflux;

(C) adding about 1 to about 2.5 equivalents of $Br_2$ to said mixture per equivalent of said metachloroalkylbenzene;

(D) after said bromine has reacted and formed HBr, adding chlorine to said mixture to react with said HBr and form additional bromine; and (E) heating said mixture to a temperature above the boiling point of said parachloroalkylbenzene isomer but below the boiling point of said brominated metachloroalkylbenzene.

13. A method according to claim 12 wherein said Friedel-Crafts catalyst is ferric chloride.

14. A method according to claim 12 wherein said mixture includes about 0.01 to about 1 wt % of a cocatalyst.

15. A method according to claim 12 wherein R is ethyl.

16. A method according to claim 12 wherein liquid bromine is used in step (C).

17. A method of separating the meta isomer of an alkylbenzene having the general formula

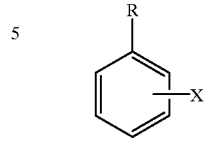

from a mixture with at least one other isomer, where X is Cl or Br and R is alkyl from $C_2$ to $C_{12}$ or cycloalkyl from $C_3$ to $C_8$, comprising (A) adding to said mixture about 0.0001 to about 5 wt % of a Friedel Crafts catalyst;

(B) exposing said mixture to about ½ to about 10 equivalents of a brominating agent per equivalent of said meta isomer, whereby said meta isomer is preferentially brominated; and (C) heating said mixture to a temperature above the boiling point of said other isomers but below the boiling point of said brominated meta isomer.

18. A method according to claim 17, wherein X is Cl.

19. A method according to claim 17, wherein the brominating agent is liquid bromine.

20. A method according to claim 17, wherein said catalyst is ferric chloride.

21. A method according to claim 17, wherein said brominating agent is BrCl.

* * * * *